United States Patent [19]

O'Neill et al.

[11] Patent Number: 5,191,075
[45] Date of Patent: Mar. 2, 1993

[54] PROCESS FOR THE PREPARATION OF PENEMS

[75] Inventors: Brian T. O'Neill, Westbrook; Douglas Phillips, Ledyard, both of Conn.

[73] Assignee: Pfizer Inc, New York, N.Y.

[21] Appl. No.: 852,598

[22] Filed: Mar. 17, 1992

Related U.S. Application Data

[60] Division of Ser. No. 594,885, Oct. 9, 1990, which is a division of Ser. No. 378,743, Jul. 11, 1989, Pat. No. 4,992,543, which is a continuation-in-part of Ser. No. 260,141, Oct. 19, 1988, Pat. No. 4,895,940.

[51] Int. Cl.$^5$ .......................................... C07D 499/00
[52] U.S. Cl. .................................................. 540/310
[58] Field of Search ........................ 540/311, 310, 312; 514/192, 195

[56] References Cited

U.S. PATENT DOCUMENTS

| | | | |
|---|---|---|---|
| 4,272,437 | 6/1981 | Menard et al. | 260/239 A |
| 4,314,942 | 2/1982 | McCombie | 260/245.2 R |
| 4,443,373 | 4/1984 | Girijavallabhan et al. | 260/245.2 R |
| 4,443,463 | 4/1984 | McCombie | 424/270 |
| 4,530,793 | 7/1985 | Girijavallabhan et al. | 260/245.2 R |
| 4,577,016 | 3/1986 | Alpegiani et al. | 544/182 |
| 4,584,133 | 4/1986 | Girijavallabhan et al. | 260/245.2 R |
| 4,610,823 | 9/1986 | DiNinno et al. | 540/310 |
| 4,614,737 | 9/1986 | Hamanaka | 514/193 |
| 4,614,738 | 9/1986 | Girijavallabhan et al. | 514/194 |
| 4,619,924 | 10/1986 | Hamanaka | 514/195 |
| 4,631,150 | 12/1986 | Battistini et al. | 540/310 |
| 4,673,737 | 6/1987 | Evans et al. | 540/205 |
| 4,675,317 | 6/1987 | DiNinno et al. | 514/192 |
| 4,690,922 | 9/1987 | Ganguly et al. | 514/210 |
| 4,739,047 | 4/1988 | Volkmann et al. | 540/310 |
| 4,751,297 | 6/1988 | Cue, Jr. et al. | 540/357 |
| 4,769,451 | 9/1988 | Dextraze | 540/350 |
| 4,782,145 | 11/1988 | Brighty et al. | 540/214 |
| 4,895,940 | 1/1990 | O'Neill | 540/310 |
| 4,992,543 | 2/1991 | O'Neill | 540/310 |

FOREIGN PATENT DOCUMENTS

| | | |
|---|---|---|
| 199446 | 10/1986 | European Pat. Off. |
| 257419 | 3/1988 | European Pat. Off. |
| 2097786 | 5/1987 | United Kingdom |
| 2187448 | 9/1987 | United Kingdom |

OTHER PUBLICATIONS

Andrus, et al., *J. Am. Chem. Soc.* 106, 1808–1811 (1984).
Afonso, et al., *J. Am. Chem. Soc.*, 104, 6138–6139 (1982).
Barker, et al., *Tet. Letters* 28, 2283–2286 (1987).
DiNinno et al., *Tet. Letters* 23, 3535–3538 (1982).
Ganguly, et al., *J Antimic. Chemoth.* 9 (Suppl.) C1–C5 (1982).
Ghosez, et al., *Tetrahedron* 39, 2493–2503 (1983).
Girijavallabhan, et al., *J. Antibiot.* 39, 1182–1190 (1986).
Girijavallabhan et al., *Tet. Letters* 24, 3179–3182 (1983).
Leanza, et al., *Tetrahedron* 39, 2505–2513 (1983).
Marchand-Brynaert, et al., *Tet. Letters* 21, 3085–3088 (1980).
Ona, et al., *Chem. Pharm. Bull.* 33, 4382–4394 (1985).
Perrone, et al., *J. Org. Chem.* 51, 3413–3420 (1986).
Franceschi, et al., *J. Antibiotics* 36, 938–941 (1983).

*Primary Examiner*—Nicholas S. Rizzo
*Attorney, Agent, or Firm*—Peter C. Richardson; J. Trevor Lumb; Mervin E. Brokke

[57] ABSTRACT

An efficient, multistep process for the synthesis of certain 6-(1-hydroxyethyl) 2-substituted penem antibiotics from 2-[4R-(triphenylmethylthio)-3S-(1R-(dimethyl-t-butylsilyloxy)ethyl)-2-azetidon-1-yl]acetic acid esters.

19 Claims, No Drawings

PROCESS FOR THE PREPARATION OF PENEMS

CROSS-REFERENCE TO RELATED APPLICATION

This application is a division of application Ser. No. 594,885, filed on Oct. 9, 1990, which is a division of application Ser. No. 378,743, filed on Jul. 11, 1989, now U.S. Pat. No. 4,992,543, which is a continuation-in-part of application Ser. No. 260,141, filed Oct. 19, 1988, now U.S. Pat. No. 4,895,940.

BACKGROUND OF THE INVENTION

The present invention is directed to efficient multi-step processes for the preparation of compounds of the formula (6) and (6'), as shown in Scheme 3 below; and to certain of the intermediates, specified by the general formulas (8) and (9) below, which find special value in these multistep processes. The compounds of the formulas (6) and (6') are useful as precursors of the various penem antibiotics specified by the formula (7) and (7'), also shown in Scheme 3 below.

Heretofore, a number of processes have been reported for the preparation of penem antibiotics substituted at the 2-position with an alkyl group or a thioether group, $-SR^2$, as found in the formulas (6), (6'), (7) and (7') below. For thioether compounds (6) and (7), two of the more general of these processes are illustrated in Schemes 1 and 2. In Scheme 1, an alternative intermediate to the silver salt of the mercaptan is the mercaptan itself, reportedly obtained by $Zn/H^+$ reduction of the tritylated thiol (Girijavallabhan et al., *J. Antibiotics* 39, 1182 (1986); U.S. Pat. No. 4,584,133). Menard et al., U.S. Pat. No. 4,272,437, has also described processes related to those of Scheme 2, which were applied more generally to the synthesis also of the compounds (6') and (7'). For example intermediates of the type (K) are reacted with an acylating agent such as $$R^5R^6CH\text{-}COCl$$

to form compounds structurally related to (L), which in turn are heated to close the ring and thus form said compounds (6') and (7'). See also published application EP 199,446, where compounds of the type (6') and (7') below in which $R^5$ and $R^6$ are taken together are similarly prepared.

Scheme 1

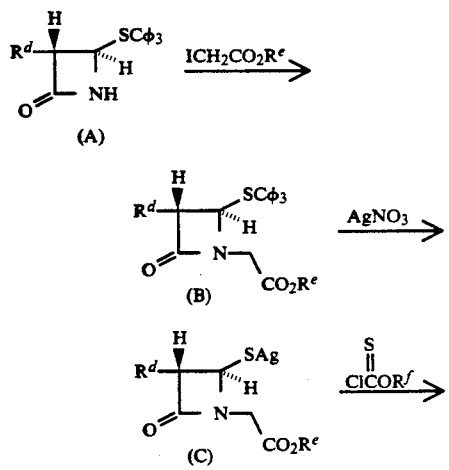

-continued
Scheme 1

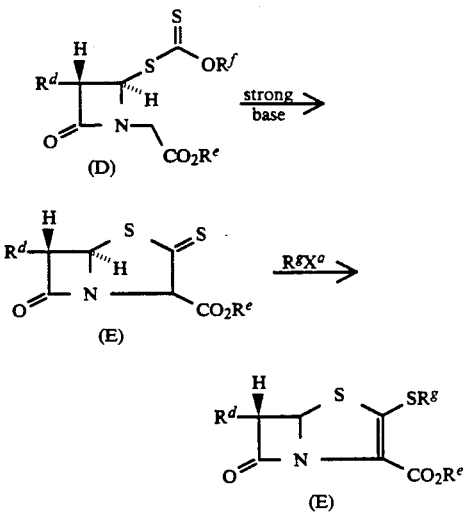

References:
Girijavallabhan et al., *J. Antibiotics* 39, 1182 (1986); U.S. Pat. No. 4,584,133, wherein

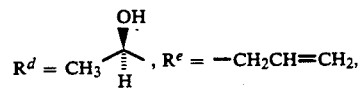
, $R^e = -CH_2CH=CH_2$, $R^f$ = beta-naphthyl, $R^g = C_2H_5$, $CH_2N$  N, etc., $X^a$ = leaving group.

DiNinno et al., U.S. Pat. No. 4,610,83 (1986); Leanza et al., *Tetrahedron* 39, 2505 (1983), wherein

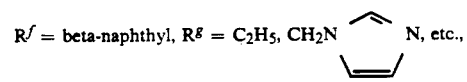
, $R^e = -CH_2CH=CH_2$ or $-CH_2\phi NO_2$, $R^f = C_6H_5$, $R^g$ = alkyl, aralkyl, etc., $X^a$ = leaving group.

See also Girijavallabhan et al., U.S. Pat. Nos. 4,443,373 and 4,530,793 for an alternative synthesis of the compounds (E), wherein $R^d$ is $CH_3CHOH$- and $R^e$ is $CH_2CH=CH_2$ or $CH_2CH_2OSi(CH_3)_3$, from the compound (A).

Scheme 2

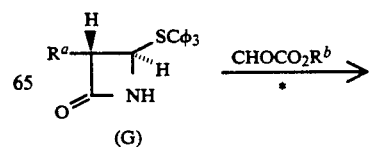

-continued
Scheme 2

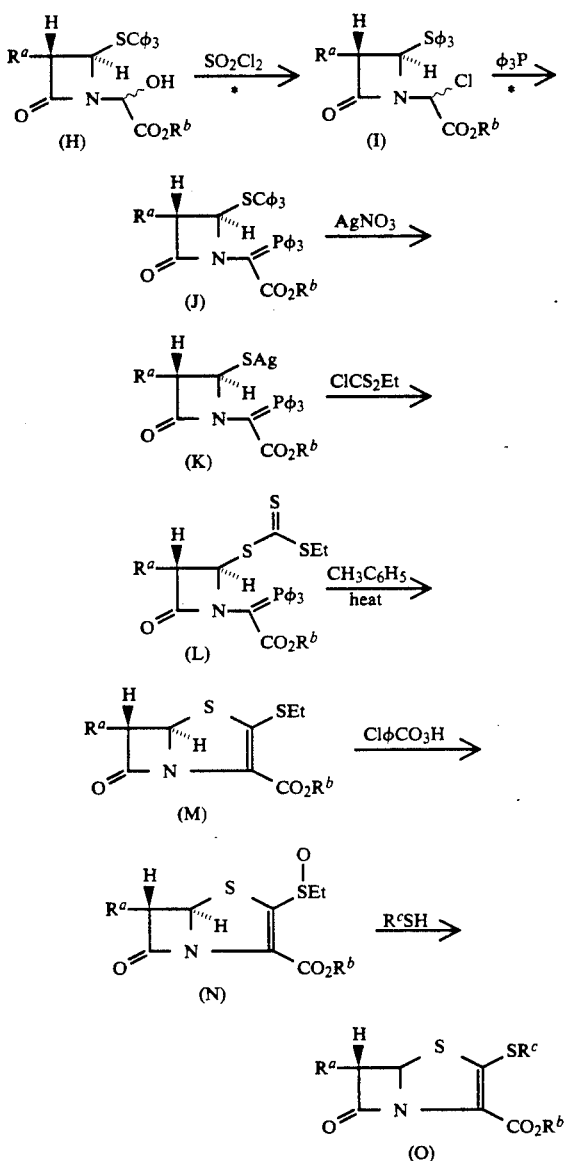

*These steps assumed on the basis of the footnote 16 reference to U.K. 2,042,514.

Reference:
DiNinno et al., *Tetrahedron Letters* 23, 3535 (1982), wherein:

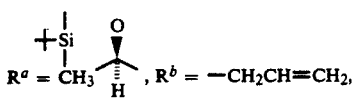

$R^c = -CH(CH_3)_2, -CH_2CH_2OH,$ etc.

See also Ganguly et al., *J. Antimicrob. Chemo.* 9, Suppl. Cl, (1982) using several similar steps in a different sequence.

Ghosez et al., *Tetrahedron Letters* 39, 2493 (1983) have described the synthesis of 2-oxopenams from penicillin G and the conversion of same to 2-alkoxypenem derivatives of penicillin G. Japanese Kokai 84-115,788 (Chem. Abst. 96:34979y, Derwent Abst. 78700 D) similarly describes conversion of hydroxy and carboxy protected 6-(1-hydroxyethyl)-2-oxopenams to the corresponding alkoxy analogs.

Additional, alternative methods for the synthesis of penems include those described by Dextraze et al., U.S. Pat. No. 4,769,451; Pirie et al., U.S. Pat. No. 4,751,297; Volkmann et al., U.S. Pat. No. 4,739,047; Brighty, U.S. Pat. No. 4,695,626; Brighty et al., U.S. Pat. No. 4,782,145; Perrone et al., *J. Org. Chem.*, 51, 3413 (1986); Batastini et al., U.S. Pat. No. 4,631,150; UK Patent application 2,187,448; Alpegiani et al., U.S. Pat. No. 4,577,016; and Franceschi et al., *J. Antibiotics* 36, 938 (1983).

There have been numerous reports in the literature concerning the conversion of 2-oxocarbapenams and 3-oxocephams to 2-(alkylthio)-2-carbapenems and 3-alkylthio-3-cephems via enolic esters:

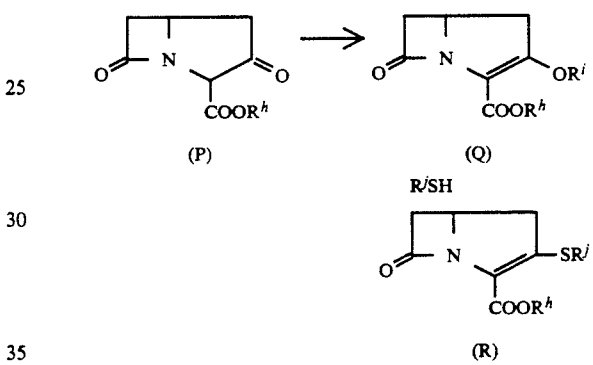

where $R^h$ is a conventional carboxy protecting group, $R^i$ is, for example, diphenyl- or diethylphosphoryl, tosyl, mesyl, or trifluoromethanesulfonyl. See for example Sletzinger et al., *Tetrahedron Letters* 21, 4221 (1980); Andrus et al., *J. Am. Chem. Soc.* 106, 1808 (1984); Evans et al., *Tetrahedron Letters* 26, 3787 (1985), and 27, 3119 (1986) and U.S. Pat. No. 4,673,737; Ratcliffe et al., 21, 31 (1980); ibid. 1979, 4947; Salzmann et al., ibid. 21, 1193 (1980); Melillo et al., ibid. 21, 2783 (1980); Iimori et al., and *J. Am. Chem. Soc.* 105, 1659 (1983). However, the chemistry observed with these carbapenem ketone groups has been generally inapplicable to the thiolactone carbonyl group of 2-oxopenems. For example, the reaction of mesyl chloride or mesyl anhydride with a compound of the type (4) below produces a compound of the type

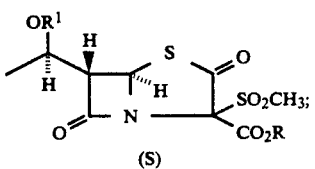

while either tosyl chloride or triflyl chloride and a compound of the type (4) produces a compound of the type:

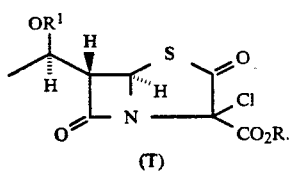

(T)

More recently it was specifically reported in published European patent application 257,419 that a compound of the type (4) below was reacted with diphenylphosphoryl chloride to form the diphenylphosphoryl ester in situ, which was in turn reacted with a phenol to form a compound of the type

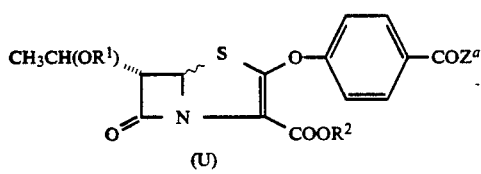

(U)

in very low yield. This application offers no specific support for the asserted broader use of other potential enol ester forming reagents such as triflyl chloride, which is in fact a known chlorinating agent, not a triflate ester forming reagent (vide supra; and Hakimelahi et al., *Tetrahedron Letters*, 1979, pp. 3643-3644).

SUMMARY OF THE INVENTION

We have now discovered an efficient multistep process for the synthesis of penem antibiotics, as summarized in Scheme 3. In particular, the present invention is directed to the processes of combined chemical steps:

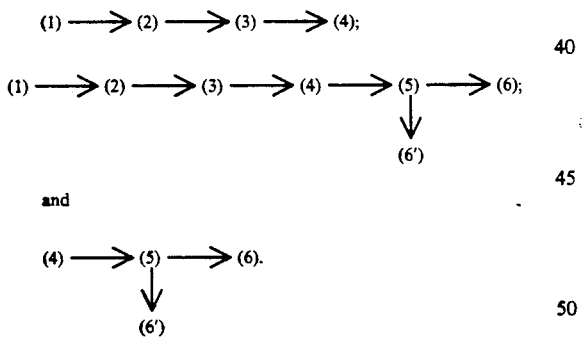

In Scheme 3, the various variable symbols are defined as follows:

R is —$CH_2CX=CH_2$, —$CH_2CH_2Si(CH_3)_3$, p-nitrobenzyl, or a conventional radical forming an ester which is hydrolyzed under physiological conditions;

X is H or Cl;

$R^1$ is a conventional silyl protecting group;

$R^2$ is a pharmaceutically acceptable radical;

$R^5$ and $R^6$ are taken separately, $R^5$ is hydrogen or ($C_1$-$C_8$) alkyl; $R_6$ is hydrogen, methyl, ($C_1C_8$)alkoxy or $OR^7$; $R^7$ is a conventional hydroxy protecting group; and $R^8$ is hydrogen, ($C_1$-$C_8$) alkoxy or OH; or $R^5$ and $R^6$ are taken together and are —$(CH_2)_mO(CH_2$-$)_p$— where m and p are each zero or an integer from 1 to 5, with the proviso that the sum of m and p is at least 3; and $R^5$ and $R^8$ correspond to $R^5$ and $R^6$, except that when $R^8$ is taken separately from $R^5$, the value $OR^7$ is replaced by OH.

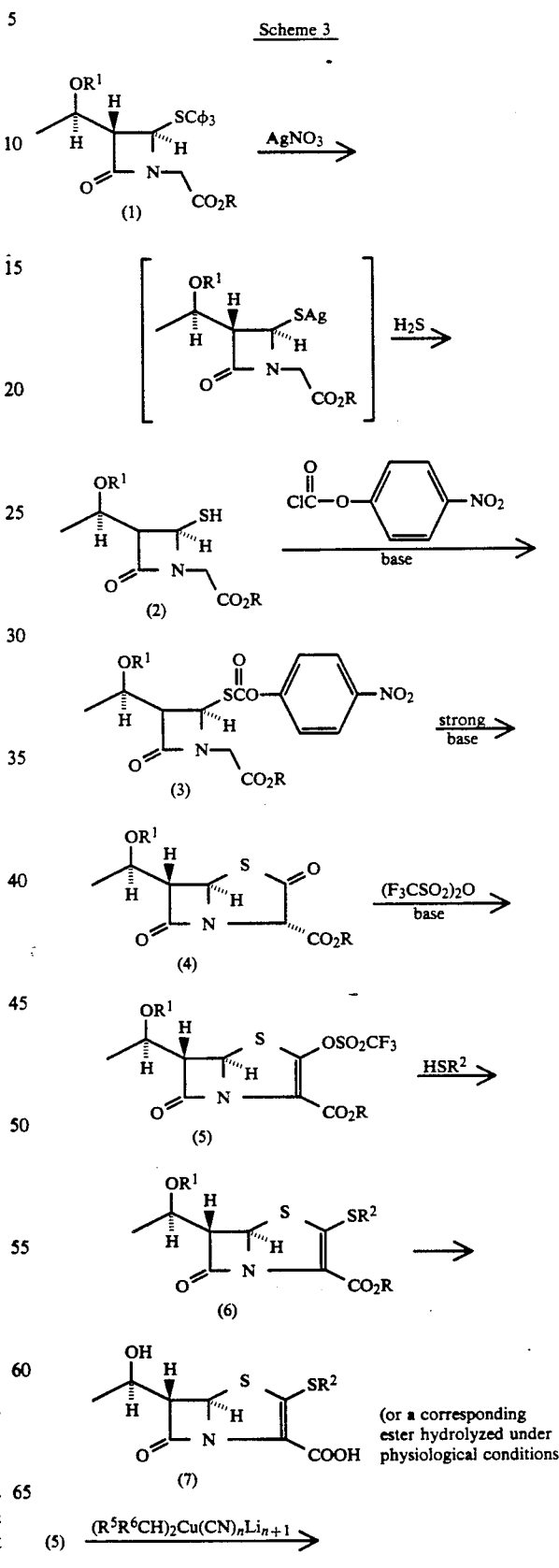

Scheme 3

-continued
Scheme 3

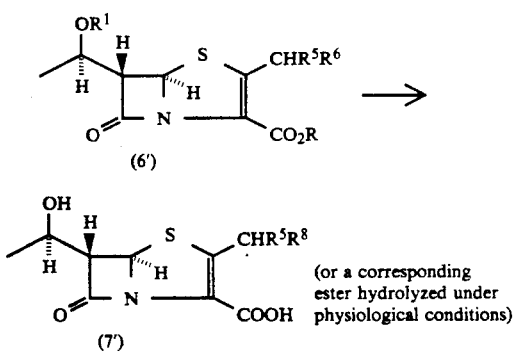

Conventional radicals which form esters which are hydrolyzed under physiological conditions have become as common in the beta-lactam art as pharmaceutically-acceptable salts. As in the case of numerous other beta-lactam antibiotics, such "pro-drug" esters are generally used orally to enhance gastrointestinal absorption. Once absorbed, they are hydrolyzed in vivo to form the corresponding penem acid. Preferred ester radicals are —$CHR^3OCOR^4$ or —$CHR^3OCO_2R^4$, where $R^3$ is hydrogen or methyl and $R^4$ is ($C_1$-$C_8$)alkyl, most particularly pivaloyloxymethyl and 1-(ethoxycarbonyloxy)ethyl.

Among the conventional silyl protecting groups are trimethylsilyl and dimethl-t-butylsilyl. The latter is most preferred for its ease of introduction and removal, while at the same time possessing excellent stability as a protecting group during the various other process steps of the present invention.

Pharmaceutically acceptable radicals $R^2$ have been extensively defined in the prior art, as will be evident from the following prior art references:
(a) Hamanaka, U.S. Pat. No. 4,614,737;
(b) Girijavallabhan et al., U.S. Pat. No. 4,614,738;
(c) Hamanaka, U.S. Pat. No. 4,619,924;
(d) Girijavallabhan et al., U.S. Pat. No. 4,443,463;
(e) Girijavallabhan et al., U.S. Pat. No. 4,530,793;
(f) Girijavallabhan et al., U.S. Pat. No. 4,584,133;
(g) Ganguly et al., U.S. Pat. No. 4,690,922;
(h) McCombie, European published application 61,205;
(i) Hamanaka, European published application 132,101;
(j) Hamanaka, European published application 138,539;
(k) Perrone et al., European published application 199,490;
(l) Takemura et al., European published application 210,883;
(m) Kirkup et al., European published application 238,285;
(n) Sunegawa et al., European published application 243,686;
(o) McCombie et al., European published application 257,602; and
(p) DiNinno et al., Tetrahedron Letters 3535 (1982).

Preferred values of $R^2$ found in the prior art (as noted by lower case letter from the list of references immediately above) are as follows:

($C_1$-$C_4$)alkyl (b, e, h, p), (1,3-dioxacyclopent-4-yl)methyl (a), (1,3-dioxacyclopent-2-yl)methyl (a), (2-oxo-1,3-dioxacyclopent-4-yl)methyl (a), (1-methyl-2-imidazolyl)methyl (i), piperidinomethyl (k), 2-hydroxyethyl (b, e, h), 2-(p-nitrobenzyloxycarbonylamino)ethyl (e, h), 2-(piperidino)ethyl (b), 2-(pyrrolidino)ethyl (b), 2-(morpholino)ethyl (b), 2-(4-(allyloxycarbonyl)piperazino)ethyl (b), 1-oxo-3-thiolanyl (cis and/or trans) (c), 1,1-dioxo-3-thiolanyl (c), 1-oxo-3-thianyl (cis and/or trans) (c), 1,1-dioxo-3-thianyl (c), 1-oxo-4-thianyl (cis and/or trans) (c), 1,1-dioxo-4-thianyl (c), 4-hydroxy-3-thiolanyl (cis and/or trans) (m), 4-hydroxy-1,1-oxo-3-thiolanyl (cis and/or trans) (m), 4-hydroxy-1,1-dioxo-3-thiolanyl (m), 4-hydroxy-3-furyl (m), 1,3-dioxacyclohex-5-yl (a), 2-oxo-1,3-dioxacyclohex-5-yl (a), 1-(p-nitrobenzyloxycarbonyl)-3-pyrrolidinyl (e, f), 2-oxo-3-pyrrolidinyl (j, o), 1-methyl-5-(dimethylaminocarbonyl)-3-pyrrolidinyl (n), 1-methyl-5-(2-(dimethylaminocarbonyl)ethyl-3-pyrrolidinyl (n), and trans-4-hydroxy-1-(benzyloxycarbonyl)-3-pyrrolidinyl (m).

The most highly preferred values of $R^2$ in the present process are —$C_2H_5$, —$CH_2CH(CH_3)_2$, —$CH_2CH_2OH$,

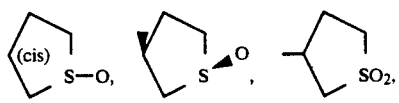

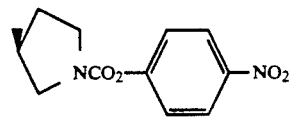

and

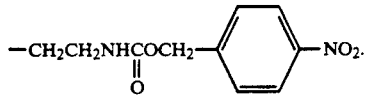

Preferred values of —$CHR^5R^8$, also found in the prior art, are methyl, hydroxymethyl, 2-tetrahydrofuryl, 2-tetrahydropyranyl or methoxymethyl. Frequently, the hydroxymethyl group is further reacted to form, for example, a carbamate.

In addition to the processes noted above, the present invention is also specifically directed to novel intermediates of the formulas (3) and (5), shown in combined form by the formula

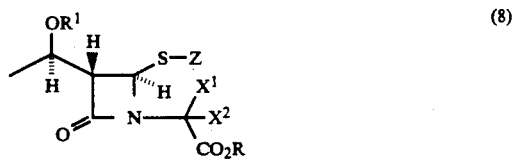

wherein
R and $R^1$ are as defined above; and
Z, $X^1$ and $X^2$ are taken together and are

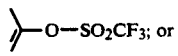

Z, $X^1$ and $X^2$ are taken separately, $X^1$ and $X^2$ are each hydrogen, and Z is p-nitrophenyloxycarbonyl; and to certain novel intermediates of the formula

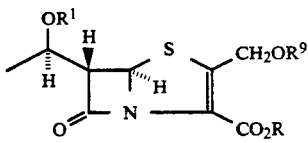

(9)

wherein R and $R^1$ are as defined above; and $R^9$ is methoxymethyl, benzyloxymethyl or 2-tetrahydropyranyl. These compounds are also encompassed by the broader formula (6') above.

DETAILED DESCRIPTION OF THE INVENTION

The present invention, which is readily carried out, provides an efficient process for penem antibiotics having the formula (7) or (7').

In the first step of this process, a triphenylmethylthio compound of the formula (1), in the presence of two or more molar equivalents of a weakly basic amine such as pyridine and in the dark, is reacted with silver nitrate (at least one molar equivalent, usually in excess, e.g., 1.5–2 molar equivalents) to produce the silver salt of the corresponding mercaptan. This reaction is generally carried out in a reaction inert solvent, such as methanol. Temperature is not critical, but lower temperatures, e.g., $-25°$ to 25° C. are generally preferred, with $0°-5°$ C. particularly convenient and satisfactory. Generally without isolation the intermediate silver salt is converted directly with excess hydrogen sulfide gas to the mercaptan. Silver is recovered as the sulfide by filtration and the mercaptan (2) recovered from the mother liquor by conventional methods such as extraction and solvent evaporation.

As used herein, the expression "reaction inert solvent" refers to a solvent which does not interact with starting materials, reagents, intermediates or products in a manner which adversely affects the yield of the desired product.

In the second step, the mercaptan (2) is reacted with substantially one molar equivalent of 4-nitrophenyl chloroformate to form the intermediate compound of the formula (3). This step is carried out in the presence of substantially one molar equivalent of a tertiary amine, preferably diisopropylethylamine and/or dimethylaminopyridine, usually in a reaction inert solvent such as tetrahydrofuran, and is preferably carried out at lower temperatures, e.g., $-25°$ to 25° C., conveniently at $0°-5°$ C. If desired, the intermediate (3) is isolated and characterized by conventional methods. However, it is preferred to simply employ the initially obtained solution of the compound of formula (3) directly in the next step.

In the third step, the intermediate (3) is cyclized in the presence of a strong base to form the desired 2-oxopenem of the formula (4), a known compound, for example, when R is allyl. Preferably, this step is carried out on a solution of the compound of the formula (3) in a reaction inert solvent such as tetrahydrofuran. The preferred strong base is lithium hexamethyldisilylamide in the same reaction inert solvent, generally used in a large molar excess (e.g., 3–5 molar equivalents). This base, conveniently purchased as a 1 M solution in tetrahydrofuran, is generally diluted (e.g., to about 0.1 to 0.2M) with tetrahydrofuran and cooled to low temperature (e.g., $-50°$ to $-100°$ C., conveniently $-78°$ C., the temperature of an acetone-dry ice bath. A solution of the compound of the formula (3) in the same solvent is added portionwise, maintaining the same low temperature. The reaction, which is substantially complete upon completion of the addition, is conveniently quenched with excess acetic acid and the 2-oxopenem (4) isolated by conventional methods of concentration and extraction.

In the next step the 2-oxopenem (4) is reacted with freshly distilled triflic anhydride, generally in slight molar excess, at reduced temperature (0° to $-90°$ C., conveniently $-78°$ C.) in a reaction inert solvent such as methylene chloride in the presence of a molar excess (generally 4–6 molar equivalents) of a tertiary amine, preferably diisopropylethylamine. If desired, the resulting enolic triflate ester of the formula (5) is isolated by chromatography of the reaction mixture on silica gel and characterized. However, this is unnecessary, the reaction solution being well-suited for direct reaction with an appropriate reagent in the next step.

In the fifth step of the present sequence, in one of its preferred embodiments, a solution of the appropriate mercaptan, $R^2SH$, conveniently dissolved in the same reaction inert solvent such as methylene chloride, is added portionwise to the cold solution of the triflate ester (5), generally allowing the temperature to rise no more than about $10°-40°$ C. from its initial value of about 0° to $-90°$ C. Upon completion of the reaction, the desired penem intermediate of the formula (6) is isolated by conventional methods, as exemplified below.

In said fifth step, in another of its preferred embodiments, a solution of the appropriate cuprous salt:

$(R^5R^6CH)_2Cu(CN)_n \, Li_{n+1}$ wherein $R^5$ and $R^6$ are as defined above and n is zero or 1, in the same or another reaction-inert solvent is reacted with triflate (5) in like-manner to produce penem intermediates of the formula (6'). However, when $R^6$ is a hydroxy protecting group, it is generally preferred to use a cuprous salt wherein n is zero.

When R is a conventional radical forming an ester which is hydrolyzed under physiological conditions, and absent an amino protecting group in the radical $R^2$, or a hydroxy protecting group in the radical $R^5R^6CH$, the penem antibiotic is obtained by conventional removal of the silyl protecting group, e.g., by methods specifically exemplified below. When R is $-CH_2CX=CH_2$, $-CH_2CH_2Si(CH_3)_3$ or p-nitrobenzyl, an additional conventional chemical step is required to form the acidic penem antibiotic of the formula (7) or (7'), or its pharmaceutically acceptable salt.

When R is $-CH_2CX=CH_2$, the group is best removed by the action of at least one molar equivalent of an alkali metal salt of an acid such as 2-ethylhexanoic acid in a reaction inert solvent such as ethyl acetate, in the presence of catalytic amounts of triphenylphosphine and tetrakis(triphenylphosphine)palladium, directly forming the alkali metal salt of the penem antibiotic. When $R^2$ contains nitrogen protected by an allyloxycarbonyl group, said group is removed by the same method.

When R is $-CH_2CH_2Si(CH_3)_3$, the group is best concurrently removed with the dimethyl-t-butylsilyl protecting group, preferably using a molar excess of tetrabutylammonium fluoride in a reaction inert solvent such as tetrahydrofuran.

When R is p-nitrobenzyl, the group is generally removed by conventional hydrogenolysis over a noble metal catalyst, preferably palladium, for example palladium-on-carbon. When R² contains a nitrogen protecting group such as benzyloxycarbonyl, said group is removed by the same method.

When the side chain contains a conventional hydroxy protecting group R⁷, it is likewise removed by conventional methods. The preferred groups of this class are methoxymethyl, benzyloxymethyl and tetrahydropyranyl, which are hydrolyzed by aqueous acid and/or hydrogenation.

The mercaptans required for the present reaction sequence are generally known or available by conventional methods. Preferred methods for the synthesis of 3S-mercaptothiolane 1R-oxide are specifically described below.

The penem antibiotics of the formula (7), as well as their pharmaceutically acceptable salts and esters, are employed in medicine according to methods described in references cited above.

It will be specifically noted that the compounds the of the formula (6) wherein R² is

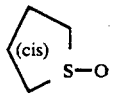

are used to prepare the corresponding product of Hamanaka, U.S. Pat. No. 4,619,924, i.e., the compound of the above formula (7), or an ester with R² of the same value. These products are a mixture of diastereoisomers, one having R² as 1R-oxo-3S-thiolanyl and the other R² as 1S-oxo-3R-thiolanyl. Of these, the 1R,3S-isomer of the formula

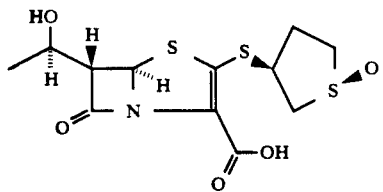

(10)

and its pharmaceutically acceptable salts and esters are preferred. This is not only because these compounds, and their several immediate precursors, are single, homogeneous compounds, such that the quality of the final products is much better controlled relative to the previously reported diastereomeric mixture (an important factor in clinical use), but because they show clinical advantages over Hamanaka's diastereomeric mixture.

The pure diastereomeric, antibacterial compound of the formula (10), its salts and its esters are tested, formulated and used according to methods detailed in above cited Hamanaka, U.S. Pat. No. 4,619,924, hereby incorporated by reference. Within the human dosage ranges there disclosed, the more preferred dosage range for these compounds is about 10-80 mg/kg/day, both orally and parenterally. These figures are illustrative only, since in some circumstances the attending physician will find it more beneficial to employ dosages outside of these ranges. In vivo hydrolyzable esters, particularly the pivaloyloxymethyl and 1-(ethoxycarbonyloxy)ethyl esters, are preferred in oral use, while the sodium or potassium salts are particularly preferred for parenteral use.

The following examples are given by way of illustration and are not to be construed as limitations of this invention, many variations of which are possible within the scope and spirit thereof.

EXAMPLE 1

Allyl 2-[4R-Mercapto-3S-(1R-(dimethyl-t-butylsilyloxy)ethyl)-2-azetidinon-1-yl]acetate A solution of 20 g (33.2 mmol) of allyl 2-[4R-(triphenylmethylthio)-3S-(1R-(dimethyl-t-butylsilyloxy)ethyl)-2-azetidinon-1-yl]acetate (Jeff et al., Tetrahedron, vol. 39, 2505-2513, 1983; U.S. Pat. No. 4,610,823) in 600 ml of methanol was cooled to 0° C. and was treated with 5.94 ml (73 mmol) of pyridine. The following portion of the reaction sequence was conducted with the reaction flask protected from light. To the solution was added solid silver nitrate (10.2 g, 60 mmol) and the reaction mixture was allowed to stir for 1.5 hours while maintained at 0° C. Once this reaction was complete, hydrogen sulfide gas was slowly introduced with constant stirring. The dark mixture was then filtered through celite with recovery of silver sulfide and the filtrate was concentrated. The organic residue was partitioned between ethyl acetate and brine. The layers were separated and the aqueous phase was reextracted with fresh ethyl acetate. The combined organic layers were dried over sodium sulfate and were then evaporated to yield title product which was used directly in the next step.

EXAMPLE 2

Allyl 2-[4R-(4-Nitrophenyloxycarbonylthio)-3S-(1R-(dimethyl-t-butylsilyloxy)ethyl)-2-azetidinon-1-yl]acetate A solution of 4.06 g (33.2 mmol) of dimethylaminopyridine and 6.69 g (33.2 mmol) of 4-nitrophenylchloroformate was prepared in 700 ml of THF. The solution was cooled to 0° C. and was treated simultaneously with a solution of the entire batch of title product from the preceding Example in 60 ml of THF, and a separate solution of 5.78 ml (33.2 mmol) of diisopropylethylamine in 60 ml of THF. The addition required 0.5 hours and formed a white precipitate. After stirring the mixture for 5 minutes, the reaction mixture was filtered with exclusion of atmospheric moisture and the filtered solution of present title product placed in a constant addition funnel and immediately used in the next step.

A portion of this solution, following filtration through a small portion of silica gel using $CDCl_3$ as eluant, was characterized by means of $^1H$-NMR (300 MHz) which showed delta: 8.22 (2H, d, J=8 Hz), 7.29 (2H, d, J=8 Hz), 5.74-5.89 (1H, ddd, J=18 Hz, 12 Hz, J=6 Hz), 5.46 (1H, d, J=2 Hz), 5.25 (1H, d, J=18 Hz), 5.17 (1H, d, J=12 Hz), 4.57 (2H, d, J=6 Hz), 4.25 (1H, dq, J=6 Hz, J=5 Hz), 4.10 (1H, d, J=19 Hz), 3.90 (1H, d, J=19 Hz), 3.27 (1H, dd, J=5 Hz, J=2 Hz), 1.26 (3H, d, J=6 Hz), 0.84 (9H, s), 0.06 (3H, s), 0.04 (3H, s).

EXAMPLE 3

Allyl
5R,6S-2-Oxo-6-[1R-(dimethyl-t-butylsilyloxy)ethyl]penam-3-carboxylate

The entire solution of the product of the preceding Example was added to 133 ml (133 mmol) of 1.0M lithium hexamethyldisilylamide (in THF) which was previously diluted with 1000 ml of THF and cooled to $-78°$ C. The addition required 0.5 hours and the solution turned bright yellow. Acetic acid (38 ml, 664 mmol) was added and the reaction mixture was stirred for 10 minutes. Approximately ½ of the solvent was removed through concentration and the remainder was diluted with diethyl ether to a volume of 2.7 liters. The ether solution was washed with saturated bicarbonate solution, saturated brine solution and then dried over sodium sulfate. The organic phase was concentrated and the residue was filtered through a pad of silica gel eluting with 15% ethyl acetate in hexane. There was obtained 6.98 g (56%) present title product as a waxy solid; m.p. $45°-48°$ C.; $^1$H-NMR(CDCl$_3$, 300 MHz)delta: 5.78-5.94 (1H, ddd, J=18 Hz, J=11 Hz, J=7 Hz), 5.51 (1H, d, J=2 Hz), 5.32 (1H, d, J=18 Hz), 5.25 (1H, d, J=11 Hz), 5.00 (1H, s), 4.65 (2H, d, J=7 Hz), 4.32 (1H, dt, J=7 Hz, J=4 Hz), 3.54 (1H, dd, J=4 Hz, J=2 Hz), 1.28 (3H, d, J=7 Hz), 0.86 (9H, s), 0.07 (3H, s), 0.05 (3H, s); C$^{13}$-NMR(CDCl$_3$, 75.43 MHz)delta: 199.0, 169.0, 163.4, 130.4, 119.6, 71.7, 67.1, 66.1, 64.6, 62.4, 25.6, 22.5, 17.9, $-4.2$, $-5.1$; m/e calculated for C$_{13}$H$_{18}$NO$_5$SSi[P-tBu]: 328.0675, found: 328.0615.

EXAMPLE 4

Allyl
5R,6S-6-[1R-(Dimethyl-t-butylsilyloxy)ethyl]-2-(trifluoromethanesulfonyloxy)penem-3-carboxylate A solution of 100 mg (0.260 mmol) of title product of the preceding Example in 5 ml of methylene chloride was treated with 0.180 ml (1.03 mmol) diisopropylethyl amine. This clear solution was then cooled to $-78°$ C. in a dry ice-acetone bath. Freshly distilled triflic anhydride (0.045 ml, 0.270 mmol) was added and the clear solution was stirred for 1 hour at $-78°$ C. to form a cold solution of present title product, which was used directly in the next step.

A small portion of this solution was purified by chromatography on silica gel followed by low temperature ($-78°$ C.) crystallization from pentane; m.p. $40°$ C.; $^1$H-NMR(CDCl$_3$, 300 MHz)delta: 5.84-5.98 (1H, ddd, J=18 Hz, J=12 Hz, J=6 Hz), 5.73 (1H, d, J=2 Hz), 5.37 (1H, dd, J=18 Hz, J=1 Hz), 5.25 (1H, dd, J=12 Hz, J=1 Hz), 4.73 (2H, dd, J=6 Hz, J-1 Hz), 4.25 (1H, dq, J=6 Hz, J=4 Hz), 3.86 (1H, dd, J=4 Hz, J=2 Hz), 1.24 (3H, d, J=6 Hz), 0.87 (9H, s), 0.08 (6H, s); m/e calculated for C$_{14}$H$_{17}$NO$_7$S$_2$SiF$_3$[P-tBu]: 460,0168, found: 460.0246.

EXAMPLE 5

Allyl
5R,6S-6-[1R-(Dimethyl-t-butylsilyloxy)ethyl]-2-[(1R-oxo-3S-thiolanyl)thio]penem-3-carboxylate A solution of 69 mg (0.388 mmol) of 3S-(acetylthio)-thiolane-1R-oxide in 5 ml of methylene chloride was treated with 5 ml of water and was cooled to 0° C. The stirred mixture was charged with 0.78 ml (1.56 mmol) of 2.0M sodium hydroxide and was allowed to stand for 0.5 hours. The reaction mixture was quenched with 0.089 ml (1.56 mmol) acetic acid and was extracted with 5×10 ml of methylene chloride. The organic phase was dried with sodium sulfate, filtered and was then treated with 0.135 ml (0.780 mmol) of diisopropylethyl amine. This solution of 3S-mercaptthiolane-1R-oxide was allowed to stand while the operation of the preceding Example was completed. It was then added to the entire cold solution of the preceding Example over 0.5 hour while maintaining the temperature below $-65°$ C. at all times. After 18 hours at $-78°$ C. the reaction mixture was treated with 10 ml of water and was allowed to warm to room temperature. The product was extracted with methylene chloride and the organic phase was washed with brine and then dried and evaporated. After filtration through silica gel, there was obtained 129 mg (98%) of present title product; m.p. $131°-134°$ C.; $^1$H-NMR(CDCl$_3$, 300 MHz)delta: 5.80-5.96 (1H, ddd, J=18 Hz, J=12 Hz, J=6 Hz), 5.62 (1H, d, J=2 Hz), 5.35 (1H, dq, J=18 Hz, J=2 Hz), 5.19 (1H, dq, J=12 Hz, J=2 Hz), 4.66 (2H, m), 4.21 (1H, dq, J=7 Hz, J=3 Hz), 3.93 (1H, dd, J=14, J=7 Hz), 3.67 (1H, dd, J=3, J=2 Hz), 3.56-3.72 (1H, m), 3.09 (1H, m), 2.54-2.84 (4H, m), 1.23 (3H, d, J=7 Hz), 0.85 (9H, s), 0.05 (6H, s); C$^{13}$-NMR(CDCl$_3$, 75.43 MHz)delta: 171.9, 159.4, 150.8, 131.7, 118.7, 118.5, 71.8, 65.7, 65.2, 64.1, 61.7, 52.7, 46.7, 33.2, 25.7, 22.5, 17.9; m/e calculated for C$_{17}$H$_{24}$NO$_5$S$_3$Si[P-tBu]: 446.0587, found:

EXAMPLE 6

Allyl
5R,6S-6-(1R-Hydroxyethyl)-2-[(1R-oxo-3S-thiolanyl)thio]penem-3-carboxylate A solution of 100 mg (0.198 mmol) of the title product of the preceding Example in 2 ml of dry THF and 0.114 ml of acetic acid was treated with 0.594 ml (0.594 mmol) 1M tetrabutylammonium fluoride and the solution was allowed to stir at room temperature for 18 hours. The reaction mixture was poured into a mixture of 50 ml ethyl acetate and 10 ml of water. The solution pH was adjusted to 6.4 by the addition of 20% potassium acetate in water. The organic phase was removed and the aqueous layer was washed twice more with 20 ml of ethyl acetate. The combined organic layers were dried over sodium sulfate and then evaporated. The residue was chromatographed on silica gel (32-63 microns) with 15% methanol in ethyl acetate. There was obtained 70.6 mg (92%) of present title product as a solid; m.p. $151°-155°$ C.; $^1$H-NMR(DMSO-d-6, 300 MHz)delta: 5.96 (1H, m), 5.82 (1H, d, J=3 Hz), 5.45 (1H, dd, J=18 Hz, J=3 Hz), 5.31 (1H, s), 5.29 (1H, dd, J=12 Hz, J=3 Hz), 5.78 (1H, dd, J=18 Hz, J=6 Hz), 5.65 (1H, dd, J=18 Hz, J=6 Hz), 3.77–4.12 (4H, m), 3.08 (1H, m), 2.67-2.98 (3H, m), 2.49 (1H, m), 1.23 (3H, d, J=7 Hz); C$^{13}$-NMR(DMSO-d-6, 75.43 MHz)delta: 173.5, 158.9, 153.6, 132.4, 117.6, 116.2, 71.3, 71.2, 64.6, 63.8, 60.4, 52.2, 46.3, 33.4, 21.4.

EXAMPLE 7

Sodium
5R,6S-6-(1R-Hydroxyethyl)-2-[(1R-oxo-3S-thiolanyl)thio]penem-3-carboxylate A solution of the title product of the preceding Example (30 mg, 0.077 mmol) in 1 ml of methylene chloride was treated with 0.058 ml (0.081 mmol) of sodium ethylhexanoate in ethyl acetate solution (1.39 mmol/ml). The reaction mixture was treated with 6 mg (0.0223 mmol)

triphenylphosphine and 6 mg (0.005 mmol) tetrakis(triphenylphosphine) palladium in 0.5 ml of methylene chloride. The mixture was allowed to stir for 1 hour at room temperature. Ethyl acetate (30 ml) was added and the mixture filtered to yield crude product. The latter was taken up in distilled water and treated with a small amount of activated carbon, filtered and the filtrate lyophilized to yield present title product, 10.5 mg; $^1$H-NMR(DMSO-d-6, 300 MHz)delta: 5.52 (1H, d, J=3 Hz), 5.24 (1H, brs), 3.74-3.96 (2H, m), 3.50-3.66 (2H, m), 2.88-2.98 (1H, m), 2.70-2.86 (1H, m), 2.44-2.60 (2H, obscured), 2.2-2.36 (1H, m), 1.14 (3H, d, J=7 Hz).

EXAMPLE 8

Allyl 5R,6S-6-[1R-(Dimethyl-t-butylsilyloxy)ethyl]-2-[(1,1-dioxo-3R- and 3S-thiolanyl)thio]penem-3-carboxylate A solution of 50 mg (0.129 mmol) of the title product of Example 3 at 0° C. in 4 ml of methylene chloride was treated with 0.089 ml (0.51 mmol) diisopropylethyl amine. This clear solution was then cooled to −78° C. in a dry ice-acetone bath. Freshly distilled trifluoromethanesulfonic anhydride (0.024 ml, 0.142 mmol) was added and the clear solution that resulted was stirred for 1 hour at −78° C. The resulting cold solution of Example 4 title product was treated with a solution of 19.6 mg (0.129 mmol) of racemic 3-mercaptothiolane-1,1-dioxide (Bezmenova et al., *Khim. Geterotsikl. Soedin.* 1975, 188, 2; Chem. Abstr. 1975, 170558) and 0.022 ml (0.129 mmol) diisopropylethyl amine in 1 ml of methylene chloride. Addition required 0.5 minutes and the solution temperature was kept below −70° C. at all times. After 2 hours at −78° C. the reaction mixture was allowed to warm to room temperature and was stirred overnight. The solution was then treated with 10 ml of water and was extracted with ethyl acetate. The organic phase was washed with brine and then dried and evaporated. After filtration through silica gel (3:2 hexane:ethyl acetate), there was obtained 66.7 mg (100%) present title product as a mixture of diastereomers. These diastereomers were separated by chromatography on silica gel by eluting with a solution of 6:3:1 hexane:ethyl acetate:benzene. The more polar diastereomer had the following properties: m.p. 180°-181° C., [alpha]$_D$= +57.14° (c=0.49 g/100 ml); HRMS calculated for C$_{17}$H$_{24}$NO$_6$S$_3$Si: 462.0536 (P-tBu), found: 462.0473. The less polar diastereomer had the following properties: m.p. 169°-170° C. [alpha]$_D$= +111.78° (c=0.73 g/100 ml); HRMS calculated for C$_{17}$H$_{24}$NO$_6$S$_3$Si: 462.0536 (P-tBu), found: 462.0506.

The blocking groups are removed from these compounds according to the methods of Examples 6 and 7 to yield the known products of Hamanaka, U.S. Pat. No. 4,619,924.

EXAMPLE 9

Allyl 5R,6S-6-[1R-(Dimethyl-t-butylsilyloxy)ethyl]-2-(ethylthio)penem-3-carboxylate Title product of Example 3 (100 mg, 0.262 mmol) was converted to a cold solution of title product of Example 4 according to the method of Example 4. This solution, at −78° C., was treated with a solution of 0.096 ml (1.3 mmol) ethanethiol and 0.226 ml (1.3 mmol) diisopropylethylamine in 1 ml of acetonitrile. Addition required 0.5 minutes and the solution temperature was kept below −70° C. during this time. After 5 minutes at −78° C. the reaction mixture was allowed to warm to 0° C. and was stirred for 2 hours. The solution was then treated with 10 ml of water and was extracted with ethyl acetate. The organic phase was washed with brine and then dried and evaporated. After filtration through silica gel (4:1 hexane:ethyl acetate) there was obtained 110 mg of present title product; m.p. 83°-84° C.; HRMS calculated for C$_{19}$H$_{31}$NO$_4$S$_2$Si: 429.1464, found: 429.1026; a compound earlier reported in racemic form by Leanza et al. Tetrahedron, vol. 39, 2505-2513 (1983).

Present title compound is deblocked according to Examples 6 and 7 to form the corresponding known penem antibiotic previously reported by Gangaly et al., *J. Antimicrobiol. Chemotherapy*, vol. 9, pp. C1-C5 (1982).

EXAMPLE 10

Allyl 5R,6S-6-[1R-Dimethyl-t-butylsilyloxy)ethyl]-2-(isopropylthio)penem-3-carboxylate By the methods of the preceding Example, title product of Example 3 (105.3 mg, 0.274 mmol) and isopropyl mercaptan (0.239 ml, 1.37 mmol) were converted to present title product, purified by chromatography on silica gel using 19:1 hexane:ethyl acetate as eluant, 60 mg, m.p. 104°-106° C.; previously known in racemic form, Leanza et al., loc. cit.; deblocked by the methods of Examples 6 and 7 to yield the corresponding, known penem antibiotic, Ganguly et al., loc. cit.

EXAMPLE 11

Allyl 5R,6S-6-[1R-(Dimethyl-t-butylsilyloxy)ethyl-2-[(hydroxyethyl)thio]penem-3-carboxylate By the methods of Example 8, the title product of Example 3 (61 mg, 0.158 mmol) and 2-mercaptoethanol (0.012 ml, 0.174 mmol) were converted to present title product, purified by chromatography on silica gel using 3:2 hexane:ethyl acetate as eluant, 60 mg; m.p. 80° C.; [alpha]$_D$= +160.4° (c=2.22 g/100 ml); HRMS calculated for C$_{19}$H$_{31}$NO$_5$S$_2$Si: 445.1412, found: 445.1420.

EXAMPLE 12

Allyl 5R,6S-6-[1R-(Dimethyl-t-butylsilyloxy)ethyl]-2-[2-(4-nitrobenzyloxycarbonylamino)ethylthio]penem-3-carboxylate By the methods of the preceding Example, the title product of Example 3 (49.5 mg, 0.129 mmol) and 2-[(4-nitrobenzyloxycarbonyl)amino]ethyl mercaptan (33 mg, 0.129 mmol; Shinkai et al., Synthesis 1980, 924) were converted to present, chromatographed title product, 71 mg; m.p. 103°-105° C.; [alpha$_D$= +88.34° (c=3.26 g/100 ml); HRMS calculated for C$_{23}$H$_{28}$N$_3$O$_8$S$_2$Si: 566.1088 (P-tBu), found: 566.1119.

EXAMPLE 13

Allyl 5R,6S-6-[1R-(Dimethyl-t-butylsilyloxy)ethyl]-2-[1-(4-nitrobenzyloxycarbonyl)-3S-pyrrolidinylthio]penem-3-carboxylate By the methods of Example 8, the title product of Example 3 (101.7 mg, 0.264 mmol) and 3S-mercapto-1-(p-nitrobenzyloxycarbonyl)pyrrolidine (0.050 ml, 0.289 mmol; Sigimura et al., Heterocycles 24, 1331, 1986) were converted to present title product which, following extraction into ethyl acetate, was purified by chromatography on silica gel using 2:1 hexane:ethyl acetate as eluant, 147 mg; m.p. 105°-106° C.; [alpha]$_D$=+260° (c=0.84, CHCl$_3$).

EXAMPLE 14

2-(Trimethylsilyl)ethyl 5R,6S-2-Oxo-6-[1R-(Di-methyl-t-butylsilyloxy)ethyl]-penem-3-carboxylate By the methods of Examples 1-3 above, 2-(trimethylsilylethyl 2-[4R-(triphenylmethylthio)-3S-(1S-(dimethyl-t-butylsilyloxy)ethyl)-2-azetidinon-1-yl]acetate was converted to present title product; $^1$H-NMR(CDCl$_3$, 300 MHz)delta: 5.52 (1H, d, J=3 Hz), 4.96 (1H, s), 4.35 (1H, q, J=8 Hz, J=5 Hz), 4.26 (2H, dt, J=12 Hz), 3.56 (1H, dd, J=5 Hz, J=3 Hz), 1.30 (3H, d, J=8 Hz), 1.06 (2H, dt, J=12 Hz), 0.89 (9H, s), 0.1 (3H, s), 0.08 (3H, s), 0.05 (9H, s); C$^{13}$-NMR (CDCl$_3$, 26.89 MHz)delta: 199.3, 169.2, 163.9, 71.8, 66.4, 65.5, 64.7, 62.5, 25.7, 22.5, 17.9, 17.4, −1.5, −4.2, −5.1; m/e calculated for C$_{15}$H$_{26}$NO$_5$SSi$_2$ [P-t-Bu]: 388.1179, found: 388.1125.

According to the sequential steps and methods of Examples 4-6, the product is further converted, via key intermediate 2-(trimethylsilyl)ethyl 5R,6S-6-[1R-(dimethyl-t-butylsilyloxy)ethyl]-2-(trifluoromethanesulfonyloxy)penem-3-carboxylate, to 2-(trimethylsilyl)ethyl 5R,6S-6-[1R-(dimethyl-t-butylsilyloxy)ethyl-]2-[(1R-oxo-3S-thiolanyl)thio]penem-3-carboxylate. The dimethyl-t-butylsilyl and trimethylsilylethyl protecting groups are removed by the action of tetrabutylammonium fluoride in THF at room temperature according to the method described in Example 8, above and Girijavallabhan et al., U.S. Pat. No. 4,443,373.

EXAMPLE 15

Pivaloyloxymethyl 5R,6S-6-(1R-Hydroxyethyl)-2-[(1R-oxo-3S-thiolanyl)-thio]penem-3-carboxylate By the sequential steps and methods of Examples 1-6, pivaloyloxymethyl 2-[4R-(triphenylmethylthio)-3S-(1S-(dimethyl-t-butylsilyloxy)ethyl)-2-azetidinon-1-yl]acetate is converted to present title product. The corresponding 1-(ethoxycarbonyloxy)ethyl ester is prepared in like manner.

EXAMPLE 16

Allyl 5R,6S-2-[Methoxymethoxy)methyl]-6-[1R-(dimethyl-t-butylsilyloxy)ethyl]penem-3-carboxylate Title product of Example 3 (49.8 mg, 0.129 mmol) was converted to a cold solution of triflate title product of Example 4 according to the method of Example 4. This solution was passed through a short plug of silica gel and then an equal volume of 20% ethyl acetate in hexane was used to elute the product from the silica gel. The resulting solution was evaporated in vacuo and then taken up in dry tetrahydrofuran. In a separate flask 103 mg (0.284 mmol) methoxymethoxytri-n-butyl stannane [Johnson et al., J. Org. Chem., 53, 4131 (1986)] was dissolved in 3 ml of dry tetrahydrofuran, the resulting solution cooled to −78° C., and 0.185 ml (0.297 mmol) 1.6M n-butyl lithium in hexane added dropwise over one minute. The resulting solution was allowed to stir for 10 minutes. In a third flask was prepared a clear, colorless solution of 29 mg (0.142 mmol) copper (I) bromide dimethyl sulfide complex in 2 ml of 1:1 tetrahydrofuran:diisopropyl sulfide [Hutchinson et al., J. Am. Chem. Soc., 109, 4930 (1987)]. To the solution of the copper (I) complex, cooled to −78° C., was added via a cold steel cannula the solution of the lithium reagent over a few seconds. To the resulting brown solution, at −78° C., was added the above solution of triflate with a syringe pump over 0.5 hour. After stirring for an additional hour, the reaction mixture was quenched with 1 ml of pH 7 NH$_4$Cl/NH$_4$OH buffer, then diluted with ethyl acetate and allowed to come to room temperature. The organic phase was washed with brine, dried over sodium sulfate and evaporated in vacuo. The residue was chromatographed on silica gel (15% ethyl acetate in hexane) to yield present title product. $^1$H-NMR (CDCl$_3$, 300 MHz) delta 5.9 (1H, ddd, J=17 Hz, J=12 Hz, J=6 Hz), 5.58 (1H, d, J=2 Hz), 5.4 (1H, dd, J=17 Hz, J=1 Hz), 5.25 (1H, dd, J=12 Hz, J=1 Hz), 4.88 (1H, d, J=17 Hz), 4.7 (1H, d, J=17 Hz), 4.7 (2H, s) 4.6–4.8 (2H, m), 4.23 (1H, dq, J=6.8 Hz, J=4.3 Hz), 3.7 (1H, dd, J=4.3, J=2 Hz), 3.4 (3H, s), 1.25 (3H, d, J=6.8 Hz), 0.9(9H, s), 0.1 (6H, s); IR (CHCl$_3$) 1790, 1710 cm$^{-1}$. UV (dioxane) lamda 321 nm, 250 nm. HRMS calc. for C$_{16}$H$_{24}$NO$_6$SSi 386.1087 (p -tBu), found 386.1058.

EXAMPLE 17

Sodium 5R,6S-2-Hydroxymethyl-6-(1R-1-hydroxyethyl)penem-3-carboxylate

By means of the combined hydrolytic methods of Examples 6 and 7, the title product of the preceding Example is converted to present title product.

EXAMPLE 18

Allyl 5R,6S-2-Methyl-6-[1R-(dimethyl-t-butylsilyloxy)ethyl]-penem-3-carboxylate

By the method of Example 16, title product of Example 3 (51.4 mg, 0.134 mmol) was converted to a solution of the triflate title product of Example 4 in tetrahydrofuran. In a separate flask was placed 16 mg (0.179 mmol) cuprous cyanide and one ml of dry tetrahydrofuran. The suspension was cooled to 0° C. and 0.336 ml (0.471 mmol) of 1.4M methyl lithium in tetrahydrofuran was added dropwise over 10 minutes. The resulting clear solution was allowed to stir for 0.5 hours, then cooled to −78° C. and the triflate solution prepared above added over 0.5 hour with a syringe pump. After stirring for an additional hour, the cold reaction was quenched with one ml of pH 7 NH$_4$Cl - NH$_4$OH buffer, then diluted with ethyl acetate and allowed to come to room temperature. The organic phase was washed with brine, dried over sodium sulfate and evaporated in vacuo. The residue was chromatographed on silica gel (10% ethyl acetate in hexane) to provide present title product; $^1$H-NMR (CDCl$_3$, 300 MHz) delta 5.91-5.79 (1H, ddd, J=17 Hz, J=11 Hz, J=5.5 Hz), 5.47 (1H, d, J=1.5 Hz), 5.33 (1H, dd, J=17 Hz, J=2 Hz), 5.16 (1H, dd, J=11 Hz, J=2 Hz), 4.71–4.53 (2H, m), 4.16 (1H, dq, J=6 Hz, J=5 Hz), 3.57 (1H, dd, J=5 Hz, J=1.5 Hz), 2.28 (3H, s), 1.17 (3H, d, J=6 Hz), 0.81 (9H, s), 0.01 (6H, s); IR (CHCl$_3$) 1785, 1710 cm$^{-1}$; UV (dioxane) lamda 314nm, 262 nm. [alpha]$_D^{20}$=+65.63° (c=1.34); HRMS calcd. for C$_{18}$H$_{29}$NO$_4$SS:383.1586, found 383.1610.

EXAMPLE 19

Sodium 5R,6S-2-Methyl-6-(1R-hydroxyethyl)-penem-3-carboxylate

By the hydrolytic methods of Examples 6 and 7, title product of the preceding Example is converted to present title product.

EXAMPLE 20

Substituting with the appropriate organolithium, and/or triflate 3-carboxylate ester, the methods of Example 16 and 18 are employed to prepare the following additional compounds:

allyl 5R,6S-2-[(2-tetrahydropyranyloxy)methyl]-6-[1R-(dimethyl-t-butylsilyloxy)ethyl]penem-3-carboxylate;

allyl 5R,6S-2-(benzyloxymethyl)-6-[1R-(dimethyl-t-butylsilyloxy)ethyl]penem-3-carboxylate;

allyl 5R,6S-2-(2-tetrahydrofuryl)methyl-[1R-(dimethyl-t-butylsilyloxy)ethyl]penem-3-carboxylate;

allyl 5R,6S-2-(2-tetrahydropyranyl)methyl-[1R-(dimethyl-t-butylsilyloxy)ethyl]penem-3-carboxylate;

2-chloroallyl 5R,6S-2-methyl-6-[1R-(dimethyl-t-butylsilyloxy)ethyl]penem-3-carboxylate;

2-(dimethylsilyl)ethyl 5R,6S-2-methyl-6-(1R-dimethyl-t-butylsilyloxy)ethyl]penem-3-carboxylate; and pivaloyloxymethyl 5R,6S-2-methyl-6-[1R-(dimethyl-t-butylsilyloxy)ethyl]penem-3-carboxylate.

PREPARATION 1

(R)-3-Thiolanyl p-Toluenesulfonate (R)-4-(Methylthio)1,2-butanediol (1.0 g, 7.35 mmol) and p-toluenesulfonyl chloride (3.0 g, 15.8 mmol) were combined in 10 ml of pyridine at 0°-5° C., then stirred at room temperature, at which time tlc (3:1 hexane:ethyl acetate) indicated no diol (Rf 0.1), appreciable of the diol ditosylate (Rf 0.53), some intermediate thiolanium salt (Rf 0.03) and a trace of title product (Rf 0.72). The reaction mixture was then heated at 60° C. for 8 hours, at which time tlc (5:1 hexane:ethyl acetate) indicated an appreciable amount of the desired title product (Rf 0.45), only a trace of the ditosylate (Rf 0.22), some probable thiolanium salt (Rf 0.0), and other, generally less polar impurities. The cooled reaction mixture was diluted with an equal volume of water and two volumes of ethyl acetate. The organic layer was separated, washed with saturated NaCl, dried (MgSO$_4$), stripped and the residue chromatographed on silica gel using 10:1 hexane:ethyl acetate as eluant to yield 0.1 g less polar impurities (stench!) and 0.25 g of present, purified title product; tlc Rf 0.55 (4:1 hexane:ethyl acetate); [alpha]$_D$= +15.87 (c=0.6, CH$_3$OH).

PREPARATION 2

3R-(p-Toluenesulfonyloxy)thiolane 1R-Oxide

A solution of 46.30 g (0.179 mol) title product of the preceding Preparation in 600 ml acetone, under nitrogen was cooled to 0° C. In a separate flask 61.73 g (0.100 mol) potassium peroxymonosulfate was stirred in 500 ml distilled water until clear. This was added to the acetone solution at 0° C. and the mixture allowed to warm to room temperature. After 25 minutes 75 ml of 10% (w/v) aqueous sodium sulfite was added, the acetone was evaporated, 300 ml ethyl acetate added and the aqueous layer was extracted with ethyl acetate (3×100 ml). The combined extracts were dried (MgSO$_4$) and concentrated to dryness to yield 48.57 g of crude product. The latter was purified by silica gel chromatography using 10:10:1 ethyl acetate:CH$_2$Cl$_2$:CH$_3$OH as eluant to afford purified title product, 34.67 g (71%); [alpha]$_D$= +4.26° (c=3.0, CHCl$_3$).

PREPARATION 3

3S-(Acetylthio)thiolane 1R-Oxide

In a flame-dried flask under nitrogen, 31.67 g (0.1156 mol) title product of the preceding Preparation was dissolved in 300 ml acetone and 19.81 g (0.1734 mol) potassium thioacetate was added. The mixture was heated at reflux for 3.5 hours and allowed to stir at room temperature overnight. The mixture was filtered, rinsed and washed with 500 ml acetone and the filtrate and washings were evaporated in vacuo to obtain 23.96 g of the desired product as an oil. The oil was purified by flash chromatography on a 120 mm×25 cm silica gel column eluting with 19:1 ethyl acetate:methanol collecting 125 ml fractions. Fractions 42–64 were combined and stripped to yield purified title product as an oil which crystallized on standing, 16.46 g; (80%); m.p. 51°-52° C.; [alpha]$_D$= −83.41° (c=0.86, CHCl$_3$).

Analysis calculated for C$_6$H$_{10}$S$_2$O$_2$: C, 40.4; H, 5.6%. Found: C, 40.15; H, 5.53%.

Present title product is alternatively prepared in like manner from the title product of Preparation 7 below.

PREPARATION 4

(R)-4-Chlorobutane-1,3-diol

In flame dried glassware under nitrogen, methyl (R)-4-chloro-3-hydroxybutyrate (1.00 g, 6.55 mmol was dissolved in 6.5 ml of dry tetrahydrofuran. The solution was cooled to 0° C. and a solution of lithium borohydride (178 mg, 8.19 mmol) in 4.1 ml of dry tetrahydrofuran was added by syringe over a 30 minute period, using 2 ml of tetrahydrofuran for rinse. The ice bath was removed and the solution stirred at 23° C. for 6 hours, then cooled to 0° C., quenched with 40 ml of methanol and acidified with 8 ml of saturated methanolic HCl. The mixture was stripped of solvent in vacuo and the residue treated with methanol and the reaction azeotroped (3×50 ml) to remove methyl borate and stripped to an oil (1.55 g). The latter was flash chromatographed on an 8.5 cm diameter×5 cm deep pad of silica gel gradiently eluted with CH$_2$Cl$_2$, 1:1 CH$_2$Cl$_2$:ethyl acetate and ethyl acetate to yield 0.67 g (82%) of title product as an oil; [alpha]$_D$= +24.5° (C=1.01, CH$_3$OH).

PREPARATION 5

(R)-4-Chloro-3-(methanesulfonyloxy)butyl Methanesulfonate

In a 500 ml 3-neck flask under nitrogen, title product of preceding Preparation 5.0 g, 0.040 mol) was dissolved in 150 ml of CH$_2$Cl$_2$. The solution was cooled to −20° C. Triethylamine (8.12 g, 11.2 mls, 0.080 mol) and dimethylaminopyridine (0.489 g, 0.004 mol) were added followed by mesyl chloride (9.19 g, 6.21 ml, 0.080 mol). The solution was stirred at −20° to −15° C. for one hour and then poured over 1 liter of crushed ice and stirred for ten minutes. The separated aqueous layer was extracted with methylene chloride (1×300 ml). The combined organic layers were washed with 1N HCl (1×500 ml), saturated NaHCO$_3$ (1×500 ml) and brine (1×500 ml), dried over MgSO$_4$, and stripped in vacuo to afford 9.96 g (88%) of present title product; [alpha]$_D$= +32.74 (C=1.06, CHCl$_3$).

To prepare (R)-4-chloro-3-(p-toluenesulfonyloxy)butyl p-toluenesulfonate, a molar equivalent of p-tolyl chloride is substituted for the mesyl chloride.

PREPARATION 6

(R)-3-Thiolanyl Methanesulfonate

Title product of the preceding Preparation (3.5 g, 0.0125 mol) was dissolved in 60 ml of 1:6 $H_2O:CH_3CN$ under $N_2$. Sodium sulfide nonahydrate (3.90 g, 0.050 mol) was added. After heating at 50° C. for 76 hours, the reaction mixture was diluted with 250 ml $CH_2Cl_2$, washed with $H_2O$ (1×100 ml) and then brine (1×100 ml), dried over $MgSO_4$, and stripped in vacuo to yield present title product, which was chromatographed on silica gel using $CH_2Cl_2$ followed by 9:1 $CH_2Cl_2$:ethyl acetate as eluant to yield 1.30 g (57%) of present title product; $[alpha]_D = +16.8°$ (C=3.0, $CHCl_3$).

By the same method the bis-p-tolyl ester of the preceding Example is converted to (R)-3-thiolanyl p-toluenesulfonate of Preparation 1.

PREPARATION 7

3R-(Methanesulfonyloxy)thiolane 1R-Oxide

By the method of Example 3 of published International patent application WO 88/08845, title product of the preceding Example (1.17 g, 6.42 mmol) and potassium peroxymonosulfate (Oxone; 2.21 g, 3.6 mmol) in 15 ml of acetone were converted to 0.96 g (75%) of present title product as a white solid; $[alpha]_D = +2.04°$ (C=2.94, $CHCl_3$).

We claim:

1. A process for the preparation of a compound of the formula

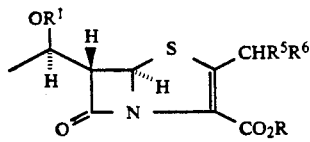

(6')

wherein
R is $-CH_2CX=CH_2$, $-CH_2CH_2Si(CH_3)_3$, p-nitrobenzyl, or a conventional radical forming an ester which is hydrolyzed under physiological conditions;
X is H or Cl;
$R^1$ is a conventional silyl protecting group; and
$R^5$ and $R^6$ are taken separately, $R^5$ is hydrogen or $(C_1-C_8)$alkyl; $R^6$ is hydrogen, methyl, $(C_1-C_8)$alkoxy or $OR^7$; and $R^7$ is a conventional hydroxy protecting group; or
$R^5$ and $R^6$ are taken together and are $-(CH_2)_mO(CH_2)_p-$ where m and p are each zero or an integer of value 1 to 5, with the proviso that the sum of m and p is at least 3;
which comprises:
(a) reacting a compound of the formula

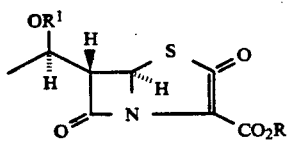

(4)

with substantially one molar equivalent of triflic anhydride in the presence of a substantial molar excess of diisopropylethylamine, in a reaction inert solvent at a temperature in the range of about $-40°$ to $-90°$ C. to form a solution of a compound of the formula

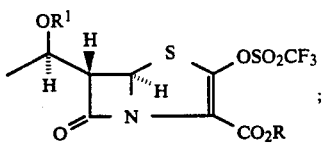

(5)

and (b) reacting said solution of the compound of the formula (5) with at least one molar equivalent of $(R^5R^6CH)_2Cu(CN)_nLi_{n+1}$ wherein $R^5$ and $R^6$ are as defined above and n is zero or 1 at a temperature in the range of about $-60°$ to $-100°$ C. to form said compound of the formula (6').

2. A process of claim 1 wherein $R^1$ is dimethyl-t-butylsilyl.

3. A process of claim 1 wherein R is a radical forming an ester group which is $-CHR^3OCOR^4$ or $-CHR^3OCO_2R^4$, where $R^3$ is hydrogen or methyl and $R^4$ is $(C_1-C_8)$alkyl.

4. A process of claim 2 wherein R is pivaloyloxymethyl or 1-(ethoxycarbonyloxy)ethyl.

5. A process of claim 2 wherein R is $-CH_2CH=CH_2$.

6. A process of claim 2 wherein R is $-CH_2CH_2Si(CH_3)_3$.

7. A process of claim 5 wherein $R^5$ and $R^6$ are taken separately and are each hydrogen.

8. A process of claim 5 wherein $R^5$ and $R^6$ are taken separately, $R^5$ is hydrogen, $R^6$ is $OR^7$ and n is zero.

9. A process of claim 8 wherein $R^7$ is methoxymethyl.

10. A process of claim 8 wherein $R^7$ is benzyloxymethyl.

11. A process of claim 8 wherein $R^7$ is 2-tetrahydropyranyl.

12. A process of claim 5 wherein $R^5$ and $R^6$ are taken together and are $-(CH_2)_3O-$.

13. A process of claim 5 wherein $R^5$ and $R^6$ are taken together and are $-(CH_2)_4O-$.

14. A process of claim 1 which further comprises preparation of said compound of the formula (4) by the further steps of:

(a) reaction of a compound of the formula

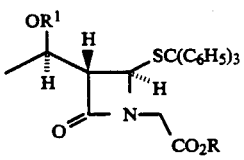

(1)

with a molar excess of $AgNO_3$ in the presence of a molar excess of pyridine in a reaction-inert solvent at a temperature in the range of about $-25°$ to $25°$ C., followed by treatment with $H_2S$, to form a compound of the formula

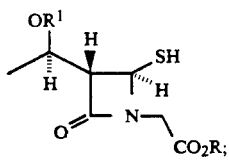
(2)

(b) acylation of said compound of the formula (2) with substantially one molar equivalent of p-nitrophenyl chloroformate in the presence of substantially one molar equivalent of 4-(dimethylamino)pyridine in a reaction-inert solvent at a temperature in the range of about $-25°$ to $25°$ C. to form a solution of a compound of the formula

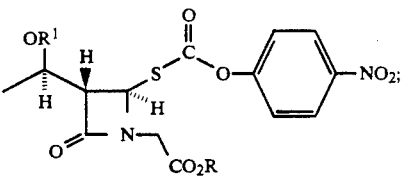
(3)

and (c) reaction of said solution of the compound of the formula (3) with a molar excess of lithium hexamethyldisilylamide at a temperature in the range of about $-50°$ to $-100°$ C. to form said compound of the formula (4).

15. A process of claim 14 wherein $R^1$ is dimethyl-t-butylsilyl.

16. A process of claim 14 wherein R is a radical forming an ester group which is $-CHR^3OCOR^4$ or $-CHR^3OCO_2R^4$, where $R_3$ is hydrogen or methyl and $R^4$ is $(C_1-C_8)$alkyl.

17. A process of claim 15 wherein R is pivaloyloxymethyl or 1-(ethoxycarbonyloxy)ethyl.

18. A process of claim 15 wherein R is $-CH_2CH=CH_2$.

19. A process of claim 15 wherein R is $-CH_2CH_2Si(CH_3)_3$.

* * * * *